United States Patent [19]

Pedersen

[11] Patent Number: 5,766,226
[45] Date of Patent: Jun. 16, 1998

[54] SWITCHED DISCHARGE PATHWAYS FOR ICD HAVING MULTIPLE OUTPUT CAPACITORS

[75] Inventor: Brad D. Pedersen, Minneapolis, Minn.

[73] Assignee: Angeion Corporation, Plymouth, Minn.

[21] Appl. No.: 761,913

[22] Filed: Dec. 9, 1996

[51] Int. Cl.$^6$ .................................. A61N 1/39
[52] U.S. Cl. ........................................ 607/5
[58] Field of Search ............................ 607/5, 7

[56] References Cited

U.S. PATENT DOCUMENTS 5,324,309  6/1994  Kallok ............................. 607/5
5,584,865  12/1996  Hirschberg et al. ............. 607/5

Primary Examiner—William E. Kamm
Assistant Examiner—George R. Evanisko
Attorney, Agent, or Firm—Brad Pedersen

[57] ABSTRACT

A high voltage output system for use with an implantable cardioverter defibrillator (ICD) system provides for switched discharge pathways utilized to achieve a windshield wiper-like output. The high voltage output system includes at least two output capacitors each having at least a separately electrically accessible one of the cathode and anode of the capacitor system. A switching control system selectively discharges the at least two capacitor systems in a repeated alternating sequence such that the one of the cathode and anode of the capacitor systems is discharged through a common electrode and the other of the cathode and anode is electrically connected for at least a portion of the discharge to a second and third defibrillation electrode, respectively. In a preferred embodiment, the cathode of each of the capacitor systems would be connected to a right ventricular (RV) defibrillation electrode, with the second and third defibrillation electrodes being a superior vena cava (SVC) electrode and a housing can (CAN) electrode. By utilizing the selectively switched discharge pathway system of the present invention, the size of the capacitor system can be reduced because the duration of the capacitive discharge is extended as a result of the alternating sequence between at least two capacitor systems, and because the heart is subjected to a more effective defibrillation countershock which continually sweeps across the heart during the capacitive discharge in a windshield wiper-like manner.

16 Claims, 4 Drawing Sheets

SWITCHED DISCHARGE PATHWAYS FOR ICD HAVING MULTIPLE OUTPUT CAPACITORS

FIELD OF THE INVENTION

The present invention relates generally to implantable cardioverter defibrillators (ICDs) and, in particular, to a method and apparatus for providing switched discharge pathways for ICDs having multiple output capacitors.

BACKGROUND OF THE INVENTION

Implantable cardioverter defibrillator (ICD) systems for the detection and treatment of cardiac arrhythmias are well known. The primary components of an ICD system include an automatic sensing system for monitoring cardiac electrical activity and sensing cardiac arrhythmias, and a high voltage output network, including a battery system, a capacitor system and control circuitry. In response to the detection of an arrhythmia, the high voltage output network will deliver a high voltage capacitive discharge electrical defibrillation countershock through a plurality of implanted electrodes. The high voltage output network utilizes a low voltage battery system connected to the primary winding of a transformer which boosts the voltage to a high voltage output that is then stored by the capacitor system and, ultimately, discharged through the implanted electrodes as a high voltage electrical countershock. Typical initial voltages for the high voltage defibrillation countershock range from 200–800 volts.

In early ICD systems, the electrical defibrillation countershock consisted of a monophasic capacitive discharge between two predetermined electrodes, typically epicardial patches sewn to the outside of the heart. In an effort to increase the effectiveness of the defibrillation countershock, numerous advances have been made to the manner in which the countershock is delivered. Presently, the preferred form of a defibrillation countershock is a biphasic waveform having a pulse duration and time constant that are optimally matched to the natural chronaxie of the heart as taught, for example, by U.S. Pat. Nos. 5,540,721 and 5,405,363. Numerous other systems have been proposed for attempting to improve the efficacy of the defibrillation countershock.

One area in which significant development has occurred is in the manner in which the defibrillation countershock is discharged through the implanted electrodes. Early attempts at controlling the discharge pathways attempted to immerse a larger portion of the heart within the electrical field of the defibrillation countershock by sequentially discharging two pulses, a first pulse discharged between a first pair of electrodes and a second pulse discharged between a second pair of electrodes, the second pair of electrodes being oriented transverse to the first pair (U.S. Pat. No. 4,708,145). More recent developments with respect to control of the discharge pathways are represented by U.S. Pat. Nos. 5,306, 291 and 5,441,518 in which the truncated discharge stored in the capacitor system is selectively apportioned among multiple discharge pathways in an attempt to optimize the defibrillation countershock waveform for a particular patient, for example.

Another area which has seen substantial development is the manner in which the defibrillation countershock is stored in and discharged from the capacitor system. Presently, all existing commercialized ICD systems utilize a pair of electrolytic (photoflash) capacitors which are arranged in series to form a single capacitor discharge system. Each of the electrolytic capacitors is capable of storing a high voltage charge of up to 375 volts, for a total effective voltage of the storage charge of 750 volts when the capacitors are arranged in series. In response to the need to improve the effectiveness of the defibrillation countershock and further decrease the overall size of the ICD system, numerous proposals to improve the capacitive system have been put forth. One such system involves the switching of the pair of electrolytic capacitors from a series configuration to a parallel configuration midway through the capacitive discharge cycle in order to further squeeze electrical charge out of the capacitor system as taught, for example, by U.S. Pat. Nos. 5,199,429 and 5,507,781. Other solutions have proposed the use of variable output capacitance as taught by U.S. Pat. No. 5,385,575, or the use of separate capacitors for the separate phases of the biphasic waveform as taught by U.S. patent application Ser. No. 08/457,307.

The use of alternative capacitor technologies than the conventional electrolytic capacitors have also been proposed. U.S. Pat. No. 5,527,346 teaches the use of higher energy density thin film capacitors in an ICD system. As taught in a corresponding patent, U.S. Pat. No. 5,391,186, the principle problem to overcome in using alternative capacitor technologies is matching the truncated capacitive discharge output of the capacitor system to the natural chronaxie of the heart. For these alternative capacitor technologies which often have smaller capacitance values (e.g., less than 60 µF), the challenge is how to extend the duration of the capacitive discharge for a time period which will match the natural chronaxie of the heart. In U.S. Pat. No. 5,391,186, one solution which is proposed to this problem is intermittently stopping the discharge through the discharge pathway so as to effectively lengthen the time over which the total discharge occurs and rely on the natural capacitance effect of the heart to "fill in the gaps" in the resulting chopped waveform. Another solution to this same problem is taught in co-pending application entitled "CAPACITOR SWITCHING OUTPUT FOR IMPLANTABLE CARDIO-VERTER DEFIBRILLATORS," Ser. No. 08/645,199, filed May 13, 1996 and assigned to the assignee of the present invention, this disclosure of which is hereby incorporated by reference. In this application a two-staged high voltage capacitive output network is taught wherein a first thin film capacitor, for example, would store the energy for the defibrillation countershock at a very high voltage (e.g. more than 2000 volts) and a second bank of smaller capacitors would be arranged to be charged in series from the first capacitor system and discharged in parallel to produce the capacitive discharge output.

While existing ICD systems have substantially improved the effectiveness of the defibrillation countershocks delivered by such systems and simultaneously reduced the overall size of the ICD system, it would be desirable to provide a system for generating a defibrillation countershock output which would further improve the effectiveness and reduce the size of the ICD system.

SUMMARY OF THE INVENTION

The present invention is a high voltage output system for use with an implantable cardioverter defibrillator (ICD) system that provides for switched discharge pathways utilized to achieve a windshield wiper-like output. The high voltage output system includes at least two output capacitors each having at least a separately electrically accessible one of the cathode and anode of the capacitor system. A switching control system selectively discharges the at least two capacitor systems in a repeated alternating sequence in which the one of the cathode and anode of the capacitor systems is discharged through a common electrode and the other of the cathode and anode is electrically connected for at least a portion of the discharge to a second and third defibrillation electrode, respectively. In a preferred embodiment, the cathode of each of the capacitor systems would be connected to a right ventricular (RV) defibrillation electrode, with the second and third defibrillation electrodes being a superior vena cava (SVC) electrode and a housing can (CAN) electrode. By utilizing the selectively switched discharge pathway system of the present invention, the size of the capacitor system can be reduced because the duration of the capacitive discharge is extended as a result of the alternating sequence between at least two capacitor systems, and because the heart is subjected to a more effective defibrillation countershock which continually sweeps across the heart during the capacitive discharge in a windshield wiper-like manner.

In a preferred embodiment of the invention, two separate electrolytic capacitors systems are connected for discharge is an alternating sequence, with each of the electrolytic capacitor systems preferably being comprised of a pair of 60 µF capacitors arranged in series. In an alternate version of this embodiment, each of the electrolytic capacitor systems is itself comprised of several capacitive sub-systems which may be separately electrically accessible such that the configuration of each of the capacitor systems may be altered by switching the configuration of the capacitor sub-systems from parallel to series configurations.

DETAILED DESCRIPTION OF THE PREFERRED EMBODIMENT

Figure 1:
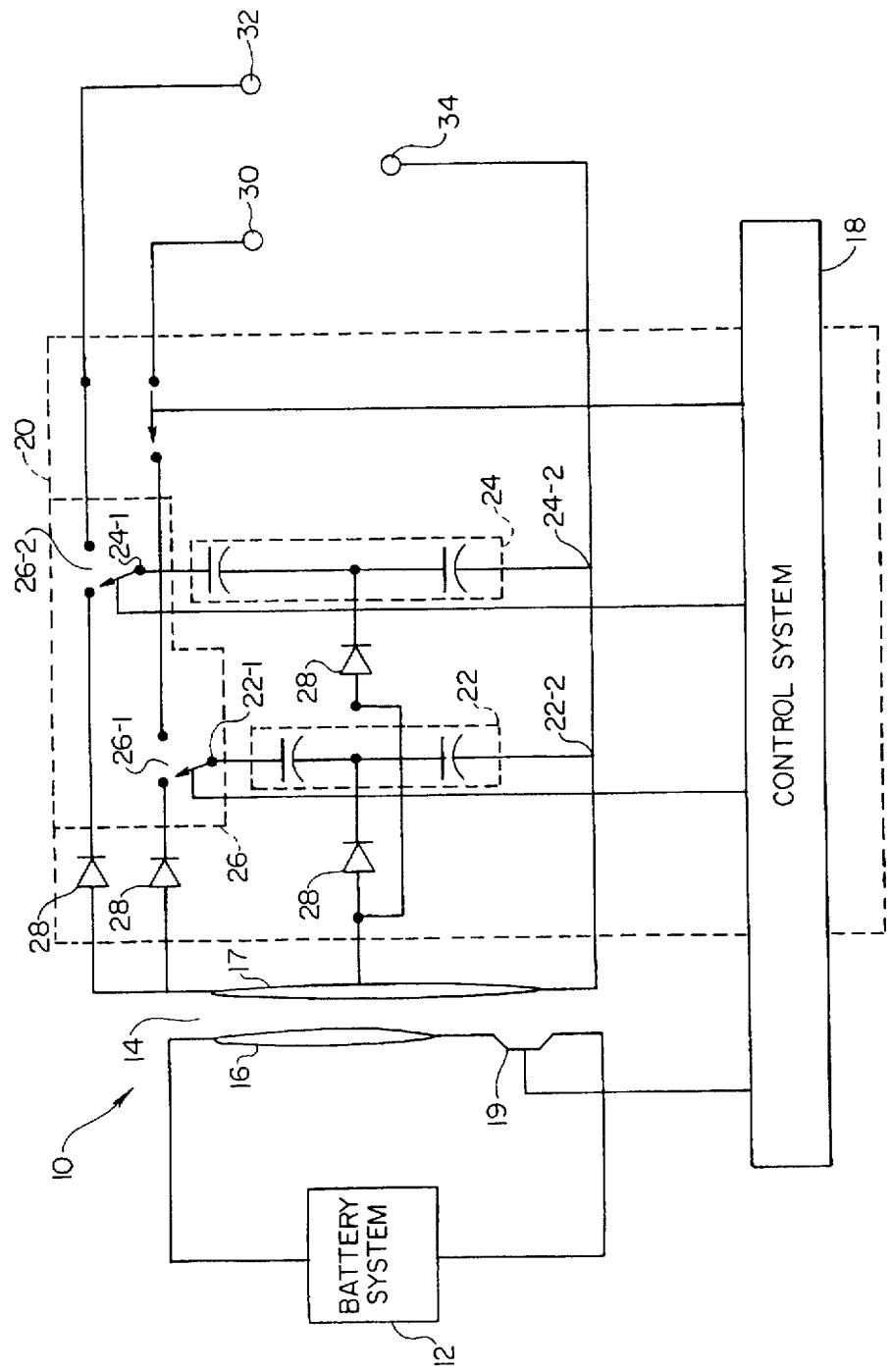
FIG. 1 is a simplified circuit diagram of an implantable cardioverter defibrillator (ICD) system in accordance with the present invention.

Referring now to FIG. 1, a simplified circuit diagram of an implantable cardioverter defibrillator (ICD) system 10 in accordance with the present invention is shown. ICD system 10 includes a battery system 12 connected to a primary winding 16 of transformer 14 for developing a high voltage across a secondary winding 17 of transformer 14. A control system 18, preferably a microcontroller or microprocessor with appropriate software and memory, is connected to a switch 19 to control operation of transformer 14. Control system 18 includes telecommunication circuitry for communicating external to the patient in which ICD system 10 is implanted, as well as appropriate sensing and detection circuitry for detecting a cardiac arrhythmia. It will be understood that the details of battery system 12, transformer 14, and control system 18, including the sensing, detection, telecommunication, and construction of ICD system 10, may be understood by reference to known ICD systems, such as described in U.S. Pat. No. 5,405,363, or such as ICD systems which are commercially available.

A high voltage output system 20 is connected to secondary winding 17 of transformer 14 High voltage output system 20 includes at least two at least two output capacitors 22, 24 and a switching control system 26. In the embodiment shown, output capacitors 22, 24 are each comprised of a pair of capacitors and diodes 28 are connected between output capacitors 22, 24 and secondary transformer 17 to establish both a center-point tap for charging output capacitor 24 and a high point tap for charging output capacitor 22. ICD system 10 also includes at least three implantable defibrillation electrodes 30, 32 and 34. Each of capacitors 22, 24 has at least a separately electrically accessible one of a cathode 22-1, 24-1 and an anode 22-2, 24-2. In the embodiment shown in FIG. 1, cathodes 22-1 and 24-1 are each separately electrically accessible via switches 26-1 and 26-2 to electrodes 30 and 32, respectively, and anodes 22-2 and 24-2 are both connected in common to electrode 34. Switches 26-1 and 26-2 are operated by control system 20 to selectively discharges the at least two capacitor systems 22, 24 in a repeated alternating sequence such that the one of the cathode 22-1, 24-1 and anode 22-2, 24-2 of the capacitor systems 22, 24 is discharged through a common one of the defibrillation electrodes, in this case electrode 34, and the other of the cathode 22-1, 24-1 and anode 22-2, 24-2 of the capacitor systems 22, 24 is electrically connected for at least a portion of the discharge to at least a second and third of the defibrillation electrodes, in this case electrodes 30 and 32 respectively.

Figure 2:
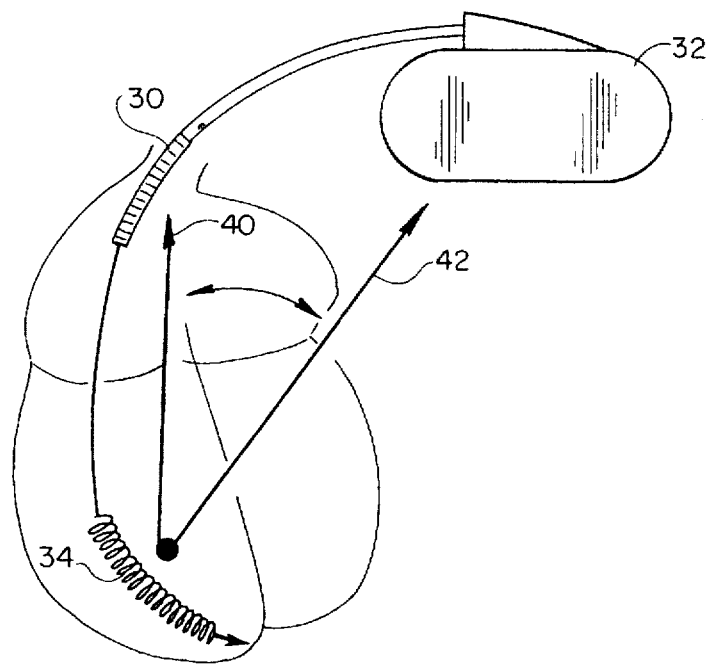
FIG. 2 is a schematic representation of a preferred embodiment of the discharge pathways of the present invention.

As shown by the schematic output in FIG. 2, control system 20 preferably includes appropriate timing logic or control circuitry to cause the combined capacitive discharge of capacitors 22, 24 to continually sweep across the heart in a windshield wiper-like manner between shock vector 40 and 42. The vectors 40 and 42 shown in FIG. 2 are generated with a right ventricular (RV) defibrillation electrode 34 as the common apex of the sweep and with the second and third defibrillation electrodes 30, 32 being a superior vena cava (SVC) electrode and a housing can (CAN) electrode. Preferably, the switching circuitry 28 causes the vectors 40 and 42 to be switched at a frequency of at least 1 KHz, and preferably at frequencies of at least 5 KHz or higher.

Figure 3:
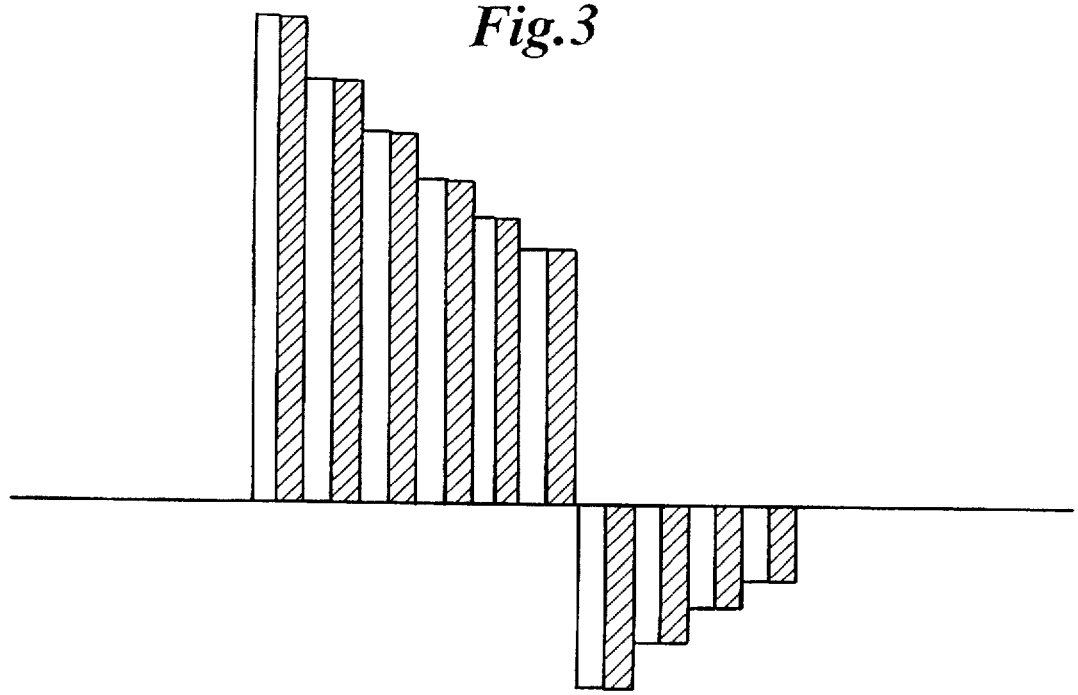
FIG. 3 is graphical representation of the discharge output of the preferred embodiment.
Figure 4:
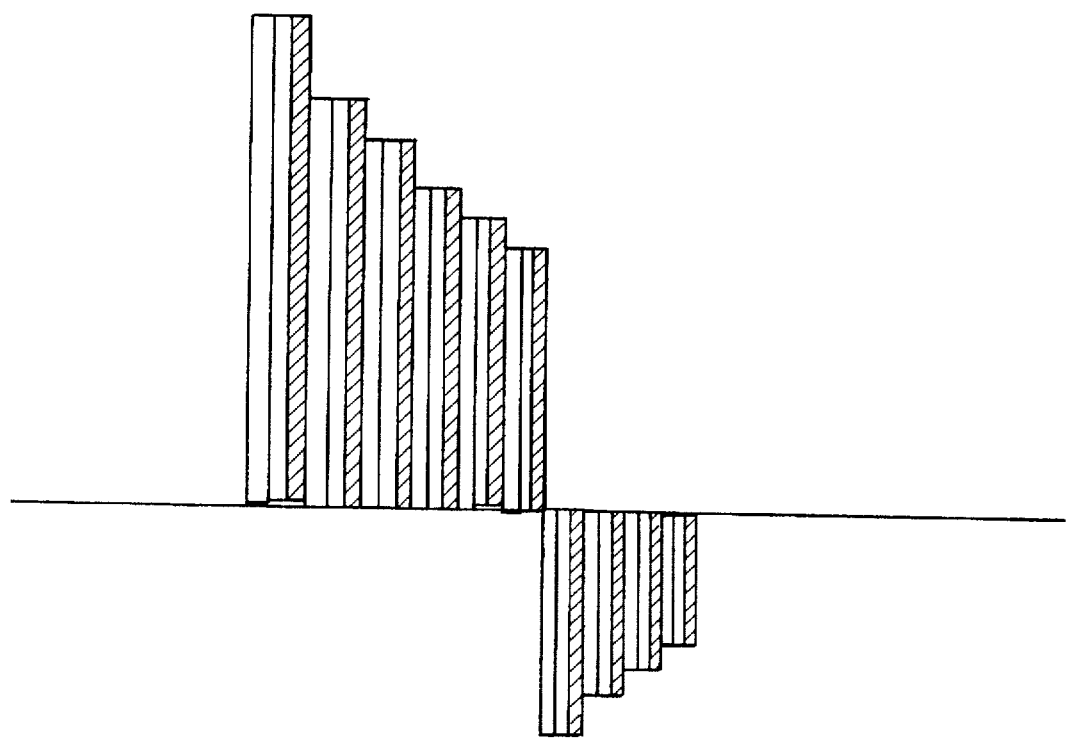
FIG. 4 is graphical representation of the discharge output of an alternate embodiment.

As shown by the representative output in FIG. 3, the duty cycle between the two shock vectors is 50%, with the portion of the defibrillation output contributed by shock vector 40 being equal in magnitude and duration to the portion of the defibrillation output contributed by shock vector 42. It will be apparent that other duty cycles could be utilized. If, for example, it is determined for a given patient that an optimum countershock should be delivered with 75% of the energy directed by the RV electrode and the CAN electrode and 25% between the RV electrode and the SVC electrode, then it is possible to utilize another switch 28 to cause the discharge of capacitor 24, for example, to be split 50% between electrodes 30 and 32 as the cathodes and electrode 34 as the anode, while the discharge of capacitor 22, for example, would be 100% between electrodes 30 as the cathode and electrode 34 as the anode. An example of this type of apportioned output is shown by the representative output in FIG. 4 in which the discharge of capacitor 24 is directed one-half to shock vector 42 and one-half to shock 40. Another alternative to apportioning the energy between the two discharges would be to utilize different charging voltages and/or capacitance values to generate different stored energies for capacitors 22, 24 so as to produce a weighted discharge output.

It will be understood that numerous variations in electrode combination are possible with the present invention. For example, a CAN electrode could be used as the common apex electrode 34, with the SVC and RV electrodes as the switched electrodes 30, 32. One or more subcutaneous (SUBQ) electrodes could be substituted for, or used in addition to, a CAN electrode, for example. Similarly, a coronary sinus (CS) electrode could be substituted for, or used in addition to the SVC electrode. Polarity reversal among the electrodes 30, 32 and 34 is also possible, either during delivery (i.e., so as to generate a biphasic waveform), with independently controllable discharge pathways as taught, for example, by U.S. Pat. No. 5,441,518, or between successive shocks in a sequence of shocks delivered as part of a preprogrammed therapy regimen as taught, for example, by U.S. Pat. No. 5,531,764. The invention also has applicability to the use of a pretreatment pulse, such as taught by U.S. Pat. No. 5,366,485 in which the wind-shield wiper effect could be utilized with the pretreatment pulses, in addition to the defibrillation pulse.

Figure 5:
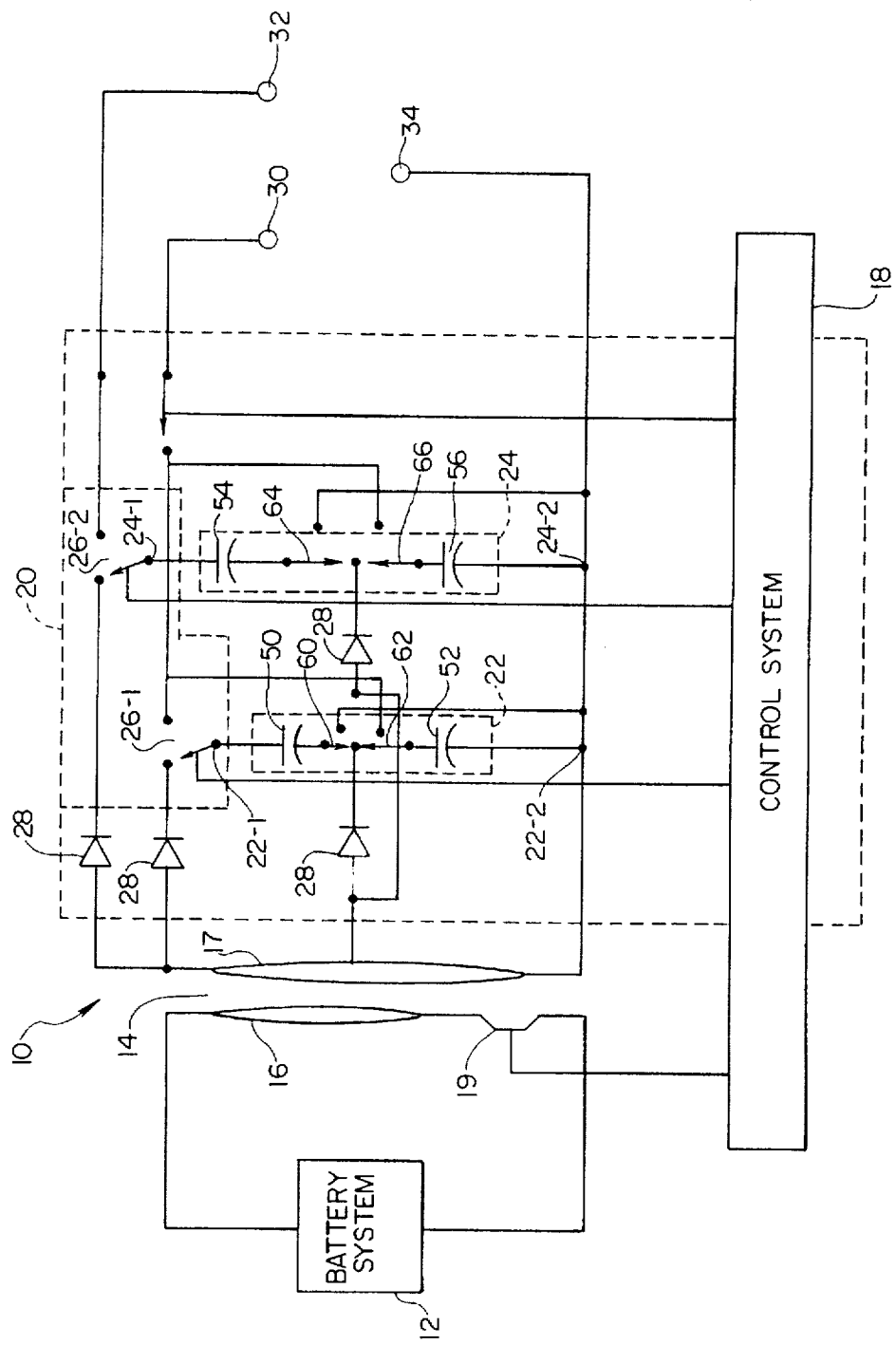
FIG. 5 is a simplified schematic diagram of an alternate embodiment of the present invention.

In the preferred embodiment of the invention as shown in FIG. 1, the two separate electrolytic capacitors systems 22, 24 are connected for discharge in an alternating sequence, with each of the electrolytic capacitor systems preferably being comprised of a pair of 60 µF capacitors arranged in series and each selectively chargable to a maximum voltage of about 375 V. In an alternate version of this embodiment as shown in FIG. 5, each of the capacitor systems 22, 24 is itself comprised of several capacitive sub-systems 50, 52, 54, 56 which may be separately electrically accessible through switches 60, 62, 64 and 66 of switch network 24 such that the configuration of each of the capacitor systems may be altered by switching the configuration of some of the capacitor sub-systems 50, 52, 54 and 56 from parallel to series configurations, such as taught in U.S. Pat. Nos. 5,199,429 and 5,507,781. In another alternate embodiment, capacitors 22, 24 could be thin film polymer capacitors of the type described in U.S. Pat. Nos. 5,391,186 and 5,527,346.

One of the advantages of utilizing the present invention is that smaller value capacitors can be utilized to delivery of a countershock having an effective current similar to that delivered by larger capacitor systems. The concept of effective current as a more accurate measurement of the efficacy of a defibrillation countershock is described in U.S. Pat. No. 5,405,363. The major problem with smaller value capacitors (e.g., capacitor systems having an effective capacitance as viewed by the heart which results in a time constant (RC) of less than the human chronaxie) is that the capacitive discharge pulse is shorter than can be optimally consumed by the human heart. As a result, the discharge is less effective and larger total energy is required to delivery a shock having the same net defibrillation capacity in terms of effective current. By alternating delivery from at least two capacitor systems 22, 24 in accordance with the present invention, the overall duration of the capacitive discharge is extended from what would otherwise be the duration dictated by the time constant for such a smaller value capacitor.

It is believed that this advantage will become more important as the average inter-electrode resistance for nontransthoracic defibrillation declines. Presently, the average inter-electrode resistance between an endocardial RV defibrillation electrode and a housing (CAN) defibrillation electrode is estimated at about 50 ohms. It is known that the addition of SVC and/or the SUBQ electrodes will reduced the effective inter-electrode resistance and such techniques are now used when the average inter-electrode resistance of the RV/CAN combination is greater than 50 ohms. As improvements in endocardial and subcutaneous electrodes continue, it is expected that average inter-electrode resistances will continue to decrease. The net effect of such a decrease in the average inter-electrode resistance is a decrease in the overall time constant (RC) of the capacitor system, even though the capacitance value has not changed. While a capacitance value of 60 µF will have an acceptable time constant of 3 ms for a 50 ohm inter-electrode resistance, the time constant becomes an unacceptable 1.5 ms if the inter-electrode resistance is reduced to 25 ohms. By utilizing the alternate sequence discharge of the present invention, it is possible to utilize smaller capacitance value capacitors and still take advantage of a decrease in inter-electrode resistance without sacrificing efficiency of the countershock in terms of effective current.

What is claimed is:

1. A high voltage output system for use with an implantable cardioverter defibrillator (ICD) system having at least three implantable defibrillation electrodes, the high voltage output system comprising:

at least two output capacitors each having at least a separately electrically accessible one of a cathode and an anode; and a switching control system that selectively discharges the at least two capacitor systems in a repeated alternating sequence such that the one of the cathode and anode of the capacitor systems is discharged through a common one of the defibrillation electrode and the other of the cathode and anode of the capacitor systems is electrically connected for at least a portion of the discharge to at least a second and third of the defibrillation electrode, respectively such that the switching control system operates to cause the discharge to effectively continually sweep across the heart in a windshield wiper-like manner until the discharge is terminated.

2. The high voltage output system of claim 1 wherein the cathode of each of the capacitor systems is connected to a right ventricular (RV) defibrillation electrode and the second and third defibrillation electrodes are a superior vena cava (SVC) electrode and a housing can (CAN) electrode.

3. The high voltage output system of claim 1 wherein a frequency of the repeated sequence of switching is at least 1 KHz.

4. The high voltage output system of claim 3 wherein the frequency is least 5 KHz.

5. The high voltage output system of claim 1 wherein one of the capacitor systems is discharged exclusively between the common electrode and the second electrode and the other of the capacitor systems is discharged exclusively between the common electrode and the third electrode.

6. The high voltage output system of claim 1 wherein a duty cycle of the discharge of the capacitor systems between the common electrode and the second and third electrode is other than 50 percent.

7. The high voltage output system of claim 1 wherein a polarity of the common and second electrodes is reversed during the discharge.

8. The high voltage output system of claim 1 wherein a polarity of the common and second electrodes and a polarity of the common and third electrodes is reversed during the discharge.

9. An implantable cardioverter defibrillator (ICD) system including at least three implantable defibrillation electrodes, comprising:

a battery system;

a sensing system;

a transformer operably connected to the battery system;

a high voltage output system operably connected to the transformer and including at least two output capacitors each having at least a separately electrically accessible one of a cathode and an anode;

an output switching network selectively connectable to the cathode and the anode of the output capacitors and to the defibrillation electrodes; and a switching control system operably connected to the battery system and the output switching network that selectively charges the high voltage output system in response to detection of a cardiac dysrhythmia by the sensing system and discharges the at least two capacitor systems in a repeated alternating sequence such that the one of the cathode and anode of the capacitor systems is discharged through a common one of the defibrillation electrode and the other of the cathode and anode of the capacitor systems is electrically connected for at least a portion of the discharge to at least a second and third of the defibrillation electrode, respectively such that the switching control system operates to cause the discharge to effectively continually sweep across the heart in a windshield wiper-like manner until the discharge is terminated.

10. The ICD system of claim 9 wherein the cathode of each of the capacitor systems is connected to a right ventricular (RV) defibrillation electrode and the second and third defibrillation electrodes are a superior vena cava (SVC) electrode and a housing can (CAN) electrode.

11. The ICD system of claim 9 wherein a frequency of the repeated sequence of switching is at least 1 KHz.

12. The ICD system of claim 11 wherein the frequency is least 5 KHz.

13. The ICD system of claim 9 wherein one of the capacitor systems is discharged exclusively between the common electrode and the second electrode and the other of the capacitor systems is discharged exclusively between the common electrode and the third electrode.

14. The ICD system of claim 9 wherein a duty cycle of the discharge of the capacitor systems between the common electrode and the second and third electrode is other than 50 percent.

15. The ICD system of claim 9 wherein a polarity of the common and second electrodes is reversed during the discharge.

16. The ICD system of claim 9 wherein a polarity of the common and second electrodes and a polarity of the common and third electrodes is reversed during the discharge.

* * * * *